United States Patent [19]
Fox

[11] Patent Number: 5,587,397
[45] Date of Patent: Dec. 24, 1996

[54] REDUCTION OF ELEVATED BLOOD LACTATE USING TWICE-DAILY DICHLOROACETATE

[75] Inventor: Anthony W. Fox, Rancho La Costa, Calif.

[73] Assignee: Cypros Pharmaceutical Corporation, Carlsbad, Calif.

[21] Appl. No.: 488,977

[22] Filed: Jun. 8, 1995

[51] Int. Cl.$^6$ .................................................... A61K 31/19
[52] U.S. Cl. ........................................................ 514/557
[58] Field of Search .............................................. 514/557

[56] References Cited

U.S. PATENT DOCUMENTS

| | | | |
|---|---|---|---|
| 4,122,188 | 10/1978 | Stacpoole | 424/317 |
| 4,631,294 | 12/1986 | Barsan | 514/557 |

OTHER PUBLICATIONS

Crabbe, D. W., et al, "The metabolic effects of dichloroacetate," *Metabolism* 30: 1024–1039 (1981).

Evans, O. B., "Dichloroacetate tissue concentrations and its relationship to hypolactatemia and pyruvate dehydrogenase activation," *Biochem Pharmacol* 31:3124–3126 (1982).

Lukas, G., et al, "Biological disposition of sodium dichloroacetate in animals and humans after intravenous administration," *J Pharmaceut Sci* 69: 419–421 (1980).

Ribes, G., et al, "Metabolic effects of sodium dichloroacetate," *Diabetes* 28: 852–856 (1979).

Stacpoole, P. W., et al, "Toxicity of chronic dichloroacetate," *New Eng J Med* 300: 372 (1979).

Stacpoole, P.W., et al, "Dichloroacetate in the treatment of lactic acidosis," *Ann. Internal Med* 108: 58–63 (1988).

Stacpoole, P. W., "The pharmacology of dichloroacetate," *Metabolism* 38: 1124–1144 (1989).

Wells, P. G., et al, "Metabolic effects and pharmacokinetics of intravenously administered dichloroacetate in humans," *Diabetologica* 19: 109–113 (1980).

*Primary Examiner*—Phyllis G. Spivack
*Attorney, Agent, or Firm*—Patrick D. Kelly

[57] ABSTRACT

This invention discloses an improved method of reducing elevated lactic acid and lactate concentrations in patients suffering from ischemic or hypoxic crises as stroke, cardiac arrest, or heart attacks, or other conditions involving surgery, that generate unwanted increases in blood or tissue lactate concentrations. This improvement comprises administering dichloroacetate (DCA), as in the sodium salt form, less than three times daily, at suitable dosages which cause the beneficial effects of DCA to persist beyond the time when the DCA has been pharmacokinetically cleared from the blood circulating in the patient.

5 Claims, 5 Drawing Sheets

REDUCTION OF ELEVATED BLOOD LACTATE USING TWICE-DAILY DICHLOROACETATE

BACKGROUND OF INVENTION

The processes involved in "glycolysis" have been described in detail in numerous reference works on biochemistry, such as the standard textbooks entitled *Biochemistry* by A. Lehninger or L. Stryer (any edition), and in *Medical Physiology* by A. Guyton.

Briefly, in all mammalian cells, molecules of glucose (a six-carbon sugar) are continuously being broken apart in a series of enzymatic steps. This results in the formation of a three-carbon intermediate called pyruvate. Pyruvate is the dissociated (ionized) form of pyruvic acid; it predominates at physiological pH's. The reactions which create pyruvate release a relatively small amount of energy.

In cells which have sufficient oxygen supplies, a substantially larger amount of energy is generated in a second set of enzymatic reactions, in which pyruvate is metabolized all the way to carbon dioxide and water. This process is often referred to as "oxidative respiration" or "aerobic respiration". It requires and consumes oxygen as part of the process.

In cells which do not have sufficient oxygen (such as in the brain of a person suffering a stroke, in the heart muscle of someone suffering a heart attack, in someone suffering cardiac arrest, suffocation, or drowning, and to a lesser extent in the muscles of someone engaged in strenuous exercise), any reserve oxygen in affected cells is used up within a few minutes, and the cells quickly become subject to conditions of inadequate oxygen supply, at varying degrees of severity. In such "hypoxic" tissue, when there is not enough oxygen to support fully oxidative respiration, the series of enzymatic steps that consume pyruvate is diverted into a different pathway, and pyruvate is converted into lactic acid instead of carbon dioxide.

The enzymatic pathway that converts pyruvate into lactic acid is usually called anaerobic glycolysis. This series of anaerobic reactions yields substantially less energy than oxidative respiration; however, it does yield some energy, and it removes metabolites that would impede and slow the initial set of reactions that generate pyruvate from glucose. Therefore, anaerobic glycolysis is used by cells as a routine mechanism when muscles are exercised, and as a backup mechanism for providing some level of energy in crisis situations such as stroke, heart attack, cardiac arrest, or asphyxiation.

Lactic acid, a three-carbon acid, readily dissociates at physiological pH ranges, to form the lactate ion, which is negatively charged. Since lactate and lactic acid co-exist (in equilibrium concentrations) in the blood, they are referred to interchangeably herein; lactate accumulation means the same thing as lactic acid accumulation.

In healthy animals (including humans), lactate is readily converted back into glucose or pyruvate in the liver and in certain muscles (including heart muscle tissue). This prevents lactate buildup, and the levels of lactate that are normally present in blood do not cause any damage. However, in patients and animals which are severely stressed or suffering from certain diseases (such as various types of terminal cancer), or in situations involving local ischemia (i.e., inadequate blood flow, as occurs during a stroke or heart attack), abnormally high accumulations of lactate and lactic acid can damage tissue and cells, by increasing the acidity of blood or cellular fluids to levels that inhibit the functioning of various essential enzymes. In addition, lactate specifically binds to and inhibits the enzyme phosphofructokinase; this can shut down the backup process of anaerobic metabolism, thereby making an ischemic or hypoxic crisis even worse.

Therefore, an abnormal increase in lactate concentration generally can be regarded as bad for cells and tissue. It leads to a sensation of fatigue in affected muscles during exercise, and during a genuine crisis (such as a stroke or heart attack), it leads to an array of adverse effects that are generally referred to by physicians under the terms "acidosis" or "lactic acidosis". In either situation, the buildup of lactic acid in blood or tissue can be regarded as a wasteful and inefficient use of energy supplies, which becomes especially detrimental under conditions of scarcity.

In addition to the problem of wasting scarce energy supplies, lactate can also act as a toxic poison if it accumulates to severe levels. It can act directly as a neurotoxin, and it can also inhibit or poison enzymes that are crucial to glycolysis, such as phosphofructokinase. If poisoned by severe lactate buildup, phosphofructokinase cannot recover and carry out its essential glycolytic functions, even after oxygen supply is restored. This poisoning of an essential glycolytic enzyme can severely aggravate the creation of oxygen-containing "free radicals," which aggressively attack cell membranes and other biomolecules, after blood supply is restored to oxygen-starved tissue.

Accordingly, methods which can efficiently reduce the creation or accumulation of lactate in blood or tissue are useful in treating patients suffering from ischemia (inadequate blood supply) and hypoxia (inadequate oxygen supply), and in various other conditions, such as certain types of diabetes and epileptic seizures, and certain types of surgery involving cardiopulmonary bypass (i.e., so-called "heart-lung" machines).

There have been prior proposals to treat such patients with dichloroacetate (DCA), which can stimulate the oxidative removal of lactate by increasing the activity of an enzyme called pyruvate dehydrogenase (PDH). For review articles discussing the enzymatic, pharmacological, and metabolic effects of DCA, see Crabb et al 1981 and Stacpoole 1989.

In the past, proposals for using DCA to reduce lactate levels in human patients via intravenous injection or infusion have taught that DCA should be injected at least three times per day, or more frequently, since it is rapidly cleared from circulating blood in the human body. For example, in reports involving administration to humans, Curry et al 1985 used five infusions per day; Irisigler et al 1979 reported three infusions within 4 hours; Stacpoole et al 1988 used four infusions over 24 hours; and Wells 1980 reported that DCA clearance in rats is also fairly rapid (e.g., Evans 1982 and U.S. Pat. No. 4,631,294 (Barsan 1986)).

It should be noted that dogs (which are widely used in cardiac and circulatory studies) demonstrate DCA metabolic clearance rates that are markedly slower than humans or rats. For example, Wells et al 1980 reported that the half-life of DCA in humans was 31 minutes, and that DCA had been completely eliminated within 5 hours. By contrast, the half-life of DCA in dogs is reported to be 19–24 hours, which is about 40 times longer than the 0.5 hour half-life of DCA in humans (Lukas et al 1980, and Ribes et al 1979). Accordingly, dogs cannot be used as reliable models or predictors for the pharmacokinetic effects of DCA in humans.

Evans 1982 showed that in rats, DCA concentration in the liver declined rapidly with time, and that the activation of the pyruvate dehydrogenase enzyme complex by DCA also dropped off rapidly with time. These results, from tests on rats, were directly contrary to the results gathered by the Applicants in human tests, as described herein. Evans et al 1981 administered DCA orally, in 100 mg/kg doses, either once, or daily for seven days. The peak DCA concentrations observed were about 25 μg of DCA per gram of liver tissue; if liver tissue was in equilibrium with plasma (which is suggested by the rapid clearance of the drug after the cessation of DCA administration), then this is only about 25 μg/mL, which was only about 1/10 of the plasma concentration seen in human patients dosed intravenously, in the studies described below.

It also should be noted that administration of DCA to reduce ischemic or hypoxic damage has never been approved by the U.S. Food and Drug Administration for human use, except in experimental clinical trials. Accordingly, administration of DCA is not an option that is currently available to patients suffering from stroke, cardiac arrest, etc., or to physicians treating such patients, even though proposals for using DCA to treat these conditions were first published and patented more than a decade ago.

This invention discloses a new method whereby DCA may be administered less frequently than three times daily, to a patient suffering from adverse lactate buildup. This new dosage regimen is supported by two new discoveries: (1) the beneficial effects of DCA in reducing lactate concentrations persist for longer than eight hours in humans, thereby eliminating the need to administer DCA every eight hours; and (2) the beneficial effect of DCA in reducing lactate concentrations in humans persists, leading to a sustained plateau effect, even after DCA concentration has spiked and has dropped to greatly reduced or undetectable levels in the blood.

In other words, it has been shown that the beneficial effects of DCA (i.e., reducing serum lactate levels) persist beyond the period of time that the drug persists in the circulation. These discoveries can substantially facilitate the medical use of DCA in patients suffering from elevated serum and/or tissue lactate concentrations due to ischemia, hypoxia, and various other conditions.

Accordingly, one object of this invention is to disclose an improved method of administering DCA to patients in need of such therapy, in a practical and cost-efficient manner.

SUMMARY OF THE INVENTION

This invention discloses an improved method of reducing elevated lactic acid and lactate concentrations in patients suffering from ischemic or hypoxic crises (such as stroke, cardiac arrest, or heart attacks), or other conditions (including certain types of surgery) that generate unwanted increases in blood or tissue lactate concentrations. This improvement comprises administering dichloroacetate (DCA), such as in sodium salt form, less than three times daily, in a manner which allows the beneficial effects of the DCA to persist beyond the time when pharmacokinetic clearance of the DCA from the circulation has occurred.

DESCRIPTION OF THE PREFERRED EMBODIMENTS

Figure 1:
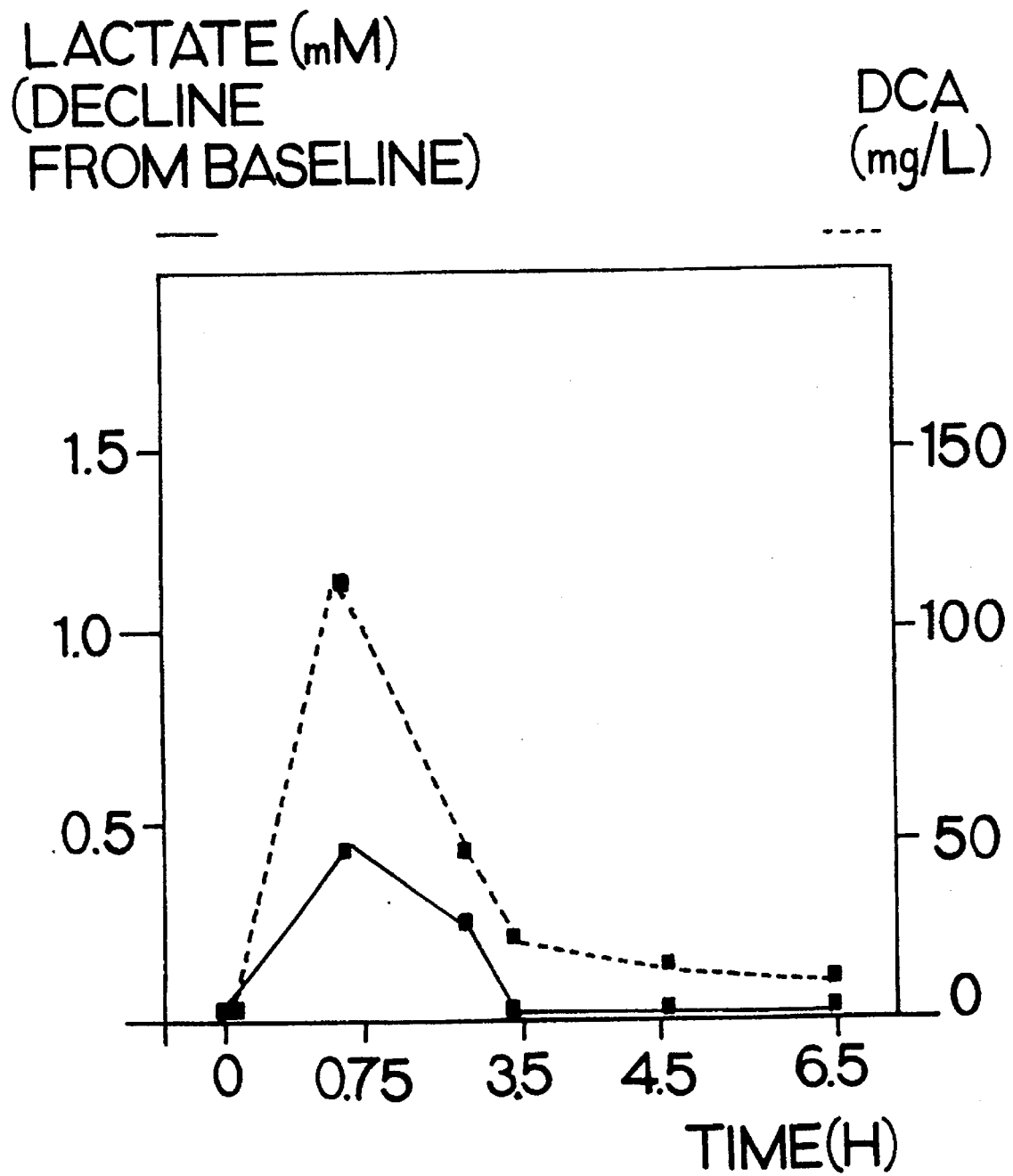
FIG. 1 is a graph depicting the conventional and previously known time-related correlation between DCA blood concentrations and blood lactate reduction, following a single infusion of 30 mg/kg DCA.

This invention discloses two useful discoveries. The first is that the beneficial effects of dichloroacetate (in a pharmacologically suitable salt, such as the sodium salt, abbreviated herein as NaDCA) can be made to persist beyond the period of time when the DCA itself is still present in the circulation, if a suitable dosage is injected into the blood of a patient. As described in Example 1, which can be regarded as prior art, administration of a conventional dosage of 30 mg/kg (i.e., 30 mg of NaDCA was injected per kilogram of patient body weight) caused a conventional and expected reduction in lactate levels; the effect lasted only a few hours, and blood lactate levels returned to normal as the DCA was cleared from the circulating blood. By contrast, as described in Example 2, when a substantially larger dosage of NaDCA was administered (60 mg/kg), the reduction in blood lactate levels lasted substantially longer and persisted even after substantially all of the DCA had been cleared from the patient's blood. As used in the claims, clearance of "substantially all" DCA from the blood refers to clearance of at least about 90% of the peak concentration of DCA that appears in the blood. The 90% level is used merely as a quantitative benchmark for interpreting the claims; in practice, injection of sufficient quantities of DCA led to lactate reductions that persisted even after DCA was no longer detectable in the blood.

This discovery led to a new and improved method of DCA administration, in which DCA is injected, twice a day, into the blood of a patient suffering from elevated blood or tissue lactate levels, at a dosage which causes a blood lactate reduction that persists for at least about 24 hours. Suitable dosage ranges are about 50 to about 100 mg/kg of the sodium salt of DCA (which is equal to about 40 to about 80 mg/kg of the DCA ion; the molecular weight of the ion, $CHCl_2COO$, is about 127 daltons, while the molecular weight of NaDCA is about 150). This improved mode of administration is contrary to the teachings of the prior art, which state that DCA should be administered to humans at least three times per day for effective reductions in blood lactate levels.

This improved method is useful for human patients suffering from any of a number of forms of ischemia or hypoxia in one or more organs, including stroke, heart attack, cardiac arrest, injury to central nervous system tissue, elevated intracranial pressure, suffocation, asphyxia, near-drowning, congenital lactic acidosis, and carbon monoxide poisoning. It is also useful for patients who are experiencing or anticipating surgery that disrupts normal blood circulation to one or more internal organs, such as surgery that requires cardiopulmonary bypass, or certain types of neurosurgery.

This new mode of administration offers a significant improvement over prior art methods, since the new method requires less time, effort, and attention by nurses or other medical care professionals. In addition, this new method of delivery requires fewer injections; this reduces (1) the number of painful skin punctures that patients must endure, (2) the number of sterilized hypodermic syringes and needles that must be used and then disposed of as hazardous medical waste; (3) the risk of blood vessel collapse following an injection or injection attempt; and (4) the amount of time and attention that must be devoted to such injections by hospital personnel, who are often overworked and hard-pressed to give every chore careful attention.

In addition, in some patients, this improved method of administration will be able to avoid the need for continuous intravenous infusion. If continuous intravenous infusion is required, it can generate various risks and complications, especially since simultaneous infusion of multiple drugs is most commonly required for patients who are severely ill or near death, in an emergency room or intensive care unit following a crisis such as a major stroke, cardiac arrest, or near-drowning.

As used herein, the terms injection, infusion, and administration are used interchangeably, to refer to various modes of introducing DCA into the bloodstream of a patient using a hypodermic needle coupled to a loaded syringe, an intravenous tube coupled to a drip bag, or any other comparable device which supplies the DCA dissolved in liquid to the needle that passes through the skin. Direct intravenous injection (i.e, introduction of the liquid directly into the bloodstream) is the strongly preferred mode of injection. Intramuscular injection is generally not as preferable as direct intravenous injection; however, intramuscular injection might be useful in some situations, as can be assessed using routine experimentation if desired. Oral and other modes of administration that do not involve transdermal injection are specifically excluded from any coverage herein. In general, intravenous administration will cause more rapid reduction in serum lactate concentration, and more rapid delivery to specific organs, than oral administration or intramuscular injection, and in patients suffering from stroke, cardiac arrest, or other ischemic or hypoxic injury or trauma, rapid access of DCA to affected tissues is generally preferred. In addition, researchers have noted that oral administration may have toxic effects, especially if administered over prolonged periods (e.g., Stacpoole et al 1979).

The sodium salt of dichloroacetate (abbreviated herein as NaDCA) is convenient and commercially available in sterile powdered form from suppliers such as TCI America (Portland, Oreg.). The sodium salt is generally preferred over the potassium salt for most patients, since potassium poses a risk of disrupting cardiac output. Several divalent salts of DCA (such as calcium or magnesium salts) are also commercially available or can be synthesized using known methods, and may be preferred for certain patients, either alone or in a mixture that also contains some of the sodium salt.

For human intravenous administration, a DCA salt must be prepared as a sterile solution. It can be stored and shipped in concentrated, powdered, or any other suitable form, provided that it is diluted, before administration, to a pH and osmotic strength which can be physiologically tolerated. Example 1 provides more information on concentrations used in tests that were carried out on human volunteers; as described therein, most solutions contained about 2% NaDCA, in near-isotonic saline carriers. However, those concentrations are not limiting, and it is anticipated that injectable formulations containing 10% or more NaDCA, up to about 15 to 20% w/v as a practical limit, dissolved in saline solution, can probably be administered safely to most patients.

The following examples further illustrate this invention. Example 1 can be regarded as depicting the prior art; it illustrates a conventional and anticipated finding, where a single injection of DCA at a dosage of 30 mg/kg reduces serum lactate in a manner that corresponds closely, over the following hours, to the persistence of DCA in the circulation. When the 30 mg.kg dosages were used as described in Example 1, blood lactate concentrations returned to normal levels within a few hours, and closely tracked the clearance of DCA from the blood.

Example 2 describes how the administration of a substantially larger infusion (60 mg/kg NaDCA) was unexpectedly found to reduce blood lactate levels in a manner that substantially outlasted the clearance of DCA from the circulation.

Example 3 showed that lactate reduction after a 100 mg/kg injection of NaDCA not only outlasted the DCA clearance process, but also lasted substantially longer than 8 hours.

Example 4 shows that the observed effects were not due to a decline in the rate of DCA clearance following a second injection. In this example, a dose of 30 mg/kg sodium dichloroacetate was administered to one set of test subjects who had not been previously injected with NaDCA, and to another set of test subjects who had been previously injected with 60 mg/kg of NaDCA, 8 hours earlier. DCA clearance rates following the 30 mg/kg injections were similar in the two groups, showing that one exposure event does not substantially alter the metabolic clearance of DCA from the blood.

Example 5 is similar to Example 4, in that it shows another similarity between DCA clearance rates in subjects who had not been previously injected with DCA, and those who had received DCA previously.

Lastly, Example 6 shows how subjects who had received an initial injection of 100 mg/kg NaDCA followed by a second injection (50 mg/kg) 8 hours later, showed reductions in serum lactate that persisted for more than 22 hours after the first infusion.

Taken together, these examples demonstrate that serum lactate may be reduced for 24 hours or more, by using only two DCA injections over a 24 hour period, provided that appropriate dosages (about 40 mg/kg DCA or more per injection) are used. These examples also demonstrate that if appropriate dosages are injected, a beneficial reduction in serum lactate levels will persist for a number of hours, even after substantially all of the DCA has been metabolically cleared from the patient's blood.

EXAMPLES

EXAMPLE 1

LACTATE REDUCTION CORRESPONDED TO DCA LEVELS AFTER A SINGLE DCA INFUSION OF 30 MG/KG

Eighteen human beings entered this study; all provided informed consent that was acceptable to an independent Institutional Review Board, which also approved the study design and toxicological coverage. The human subjects were all healthy, were fasted for 18 hours prior to the study infusions, and were all within 85% to 115% of ideal body weight, using actuarial tables published by the Metropolitan Life Insurance Company. Each received an accurately measured meal (late breakfast, 821 kcal total including 116 g of carbohydrate, 30 g of protein, and 32 g of fat).

Teflon venous catheters were placed in both forearms of all subjects. One, for drug administration, was left in place for 10 hours. The other, for blood sampling, was left in place for about 30 hours. Both venous cannulae were regularly flushed with a heparin-saline solution to avoid any risk of clogging or clotting. When blood was sampled, the first-drawn fluid was discarded, so that blood samples were not contaminated with the heparin-saline solution.

Sodium dichloroacetate (NaDCA; purchased in powdered form from TCI America, Inc., Portland, Oreg.) was dissolved in saline solution to provide a 10% sterile solution (i.e., 10 g of NaDCA in 100 ml solution) at a contract lab. The vials containing 10% solution were shipped to the study site, in Indiana, and then diluted to form approximately 2% solutions in intravenous drip bags. Exact concentrations depended to some extent on the weight of each patient; all concentrations were within 20 % of isotonic levels. A 2% solution was administered through one cannula into each test subject over a period of 30 minutes, at a dosage of 30 mg/kg (i.e, 30 milligrams of NaDCA salt per kilogram of body weight). The average total weight of NaDCA infused into each patient was about 2.26±0.54 g; total volume of solution was about 100 ml. For control subjects, a placebo saline solution having comparable sodium content was infused. Nine subjects received a single infusion of DCA, and nine received the saline placebo.

Samples of venous blood from the other cannula (in the opposite forearm) were taken, before and several times periodically after the intravenous infusion. The infusions were number-coded, and all solutions (both active and placebo) were colorless; therefore, this was a double-blinded study.

Blood samples were collected into tubes containing sodium heparin, and spun at 64 G (i.e., 64 times normal gravity) for 10 minutes, to remove blood cells. The supernatant was then deproteinized, using 6% perchloric acid; various other agents, such as acetonitrile, could alternately be used if desired. The deproteinized liquid was then centrifuged again at 64 G for 10 minutes, and the supernatant was decanted and divided into 0.20 mL aliquots. At least one aliquot was stored at $-40°$ C. as a backup in case checks were needed, while tests were run on other aliquots.

DCA assays used gas-liquid chromatography (0.20 mL sample), an electron capture detector, and a MicroVax 3100 computer for data capture (Wisconsin Analytical and Research Services, Madison, Wis.). These assays were internally and externally validated within a range of concentrations of 50 ng/mL to 5 µg/mL, with an error of the mean of 1.0% at the lower end of this range to 3.0% at the higher end of the range; during the assays, errors about a standard curve were always $-3.0\%$ to $+4.3\%$, and the standard curves were always linear within the stated range, and had correlation coefficients of 0.995 or better.

Blood samples were assayed for lactate concentration at a registered clinical laboratory (SmithKline Beckman, in Evansville, Ind.), using a commercial assay kit sold by Sigma Chemical Company (St. Louis, Mo.). This assay uses an enzymatic procedure involving lactate dehydrogenase; it adds glycine to the samples as a buffer, along with a standardized excess amount of NAD. The lactate dehydrogenase enzyme converts lactate to pyruvate, and the hydrogen atoms that are liberated by this reaction convert NAD to reduced NAD (NADH). The NADH absorbs ultraviolet light at 340 nm, and the level of absorbance (measured by a spectrophotometer) is directly proportional to the amount of NADH in the sample, and thus to the amount of lactate that was initially present in the sample.

An alternate assay for determining lactate concentrations is also available, which uses an oxidase enzyme and a peroxidase enzyme. The oxidase converts lactate to pyruvate in a manner that generates hydrogen peroxide, and the peroxidase causes any hydrogen peroxide to react with a chromogen which, in its converted state, absorbs light at 540 nm. The level of absorbance is directly proportional to the original concentration of lactate.

Test subjects that received saline placebos evidenced no DCA in their venous blood. They had serum lactate concentrations of 0.92±0.16 mM (mean value, and standard error of the mean) at baseline, and 1.01±0.23 fifteen minutes after the end of the infusion; these value were not statistically different. Placebo-treated subjects did not evidence any significant reductions in serum lactate levels during the remainder of the study. After eating the meal described above, they evidenced a brief elevation of serum lactate, to about 2.03±0.26 mM, which returned to baseline levels within about 2 hours.

Subjects who received a single infusion of DCA (30 mg/kg) as described above evidenced a peak of DCA concentration which rapidly dropped off, and a similar peak in lactate reduction which disappeared fairly rapidly; both of these peaks are shown as a function of time in FIG. 1. The alterations in serum lactate levels are shown as a decline from baseline values, in this and other examples, to more clearly display the time-dependent correlations between DCA levels and lactate levels.

When a single infusion of 30 mg/kg was administered, these human subjects evidenced a typical direct pharmacological relationship between concentration and effect. The effect on reduction of lactate levels closely paralleled (over time) the clearance of DCA from the blood. Direct relationships such as this have lead all prior researchers to suggest and use typical dosing regimens involving three or more doses per day, in order to achieve the desired results (i.e., sustained or prolonged reductions in lactate levels).

EXAMPLE 2

LACTATE REDUCTION PERSISTED AFTER DCA CLEARANCE, AFTER A DCA INFUSION OF 60 MG/KG

Figure 2:
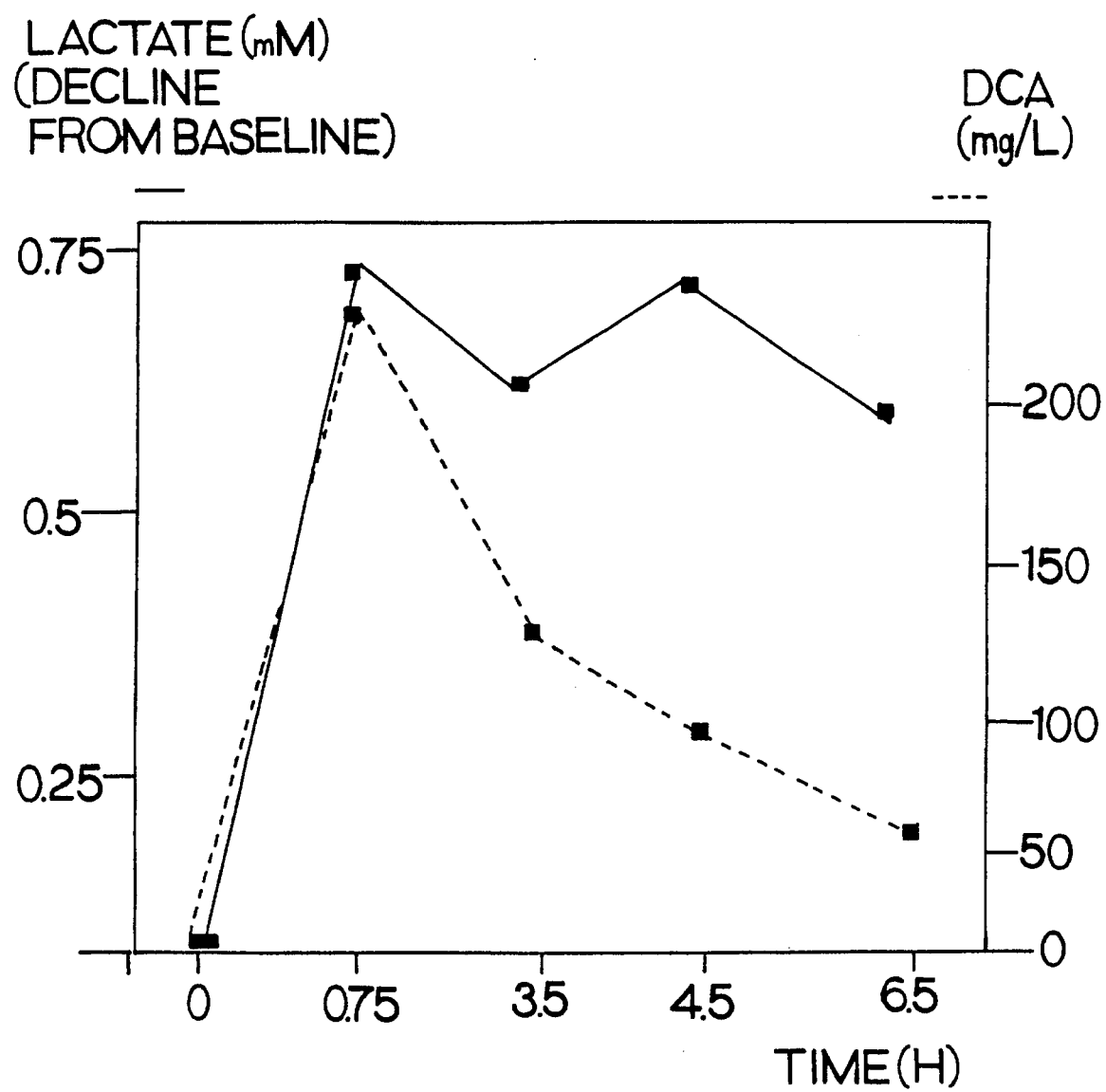
FIG. 2 is a graph depicting an unexpected and prolonged blood lactate reduction, following an infusion of a substantially higher dosage of DCA (60 mg/kg).

In a second set of test subjects (18 total: 9 test subjects and 9 saline placebo controls), sodium DCA was administered in an identical manner, using a single 30-minute infusion, at a dosage of 60 mg/kg. This test was initially intended to help generate a simple dose-response curve, but the unexpected results became part of the basis of this invention, because the time-dependent relationship between DCA concentrations and lactate reductions was discovered to be non-proportional. The physiological results of 60 mg/kg DCA infusion (i.e, reduced lactate concentrations) were found to last significantly longer than the persistence of DCA in the circulating blood. These results are shown in FIG. 2. In these tests, the reduction of serum lactate levels significantly outlasted the persistence of serum DCA levels. For example, there was no evidence of reversal of the decline in serum lactate levels at 6.5 hours and afterwards, even though nearly all of the DCA had already been avidly cleared from the blood by then, certainly to concentrations below the levels that had been shown effective in Example 1.

EXAMPLE 3

PERSISTENT LACTATE REDUCTION AFTER CLEARANCE OF 100 MG/KG DCA INFUSION

Figure 3:
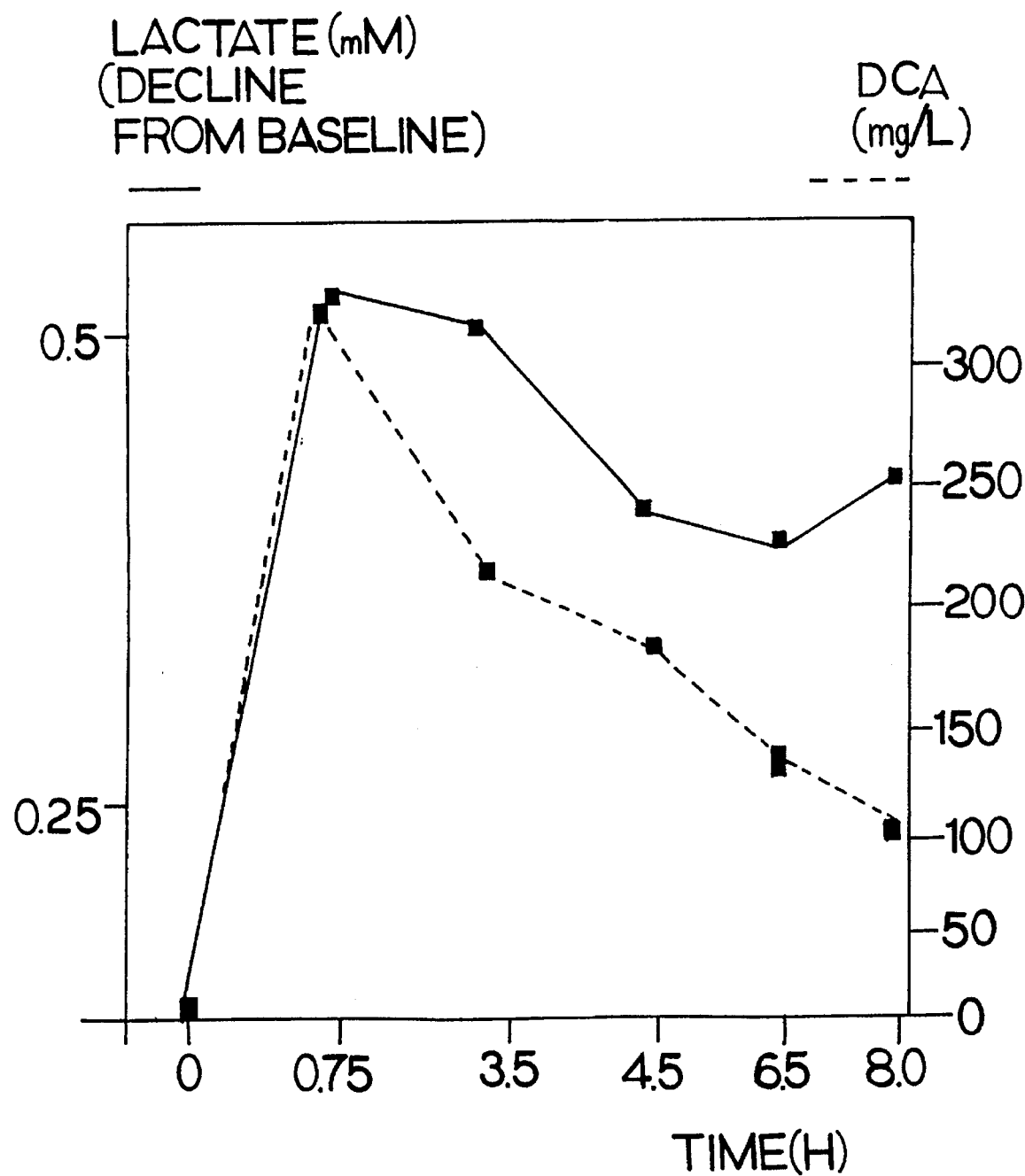
FIG. 3 depicts a prolonged blood lactate reduction which lasted more than 8 hours, following an infusion of DCA at a dosage of 60 mg/kg.

This example also depicts a persistent reduction in lactate levels after clearance of DCA from the blood. In these tests (12 subjects total: 6 DCA-tested, and 6 controls), a saline placebo or 100 mg/kg DCA was infused intravenously, as described in Examples 1 and 2. The placebo-treated controls did not evidence any DCA in their blood stream, nor any reduction in serum lactate concentration. However, as shown in FIG. 3, test subjects that were infused with 100 mg/kg dose of DCA showed a persistent reduction in serum lactate levels which significantly outlasted the serum DCA concentrations.

EXAMPLE 4

DCA CLEARANCE RATES ARE NOT AFFECTED BY PRIOR EXPOSURE TO THE DRUG

The utility of the prolonged lactate-reducing effects of DCA, which persist after the DCA has been cleared from the blood, would be limited if DCA were cleared more rapidly after a second infusion. Such increases in clearance rates occur, in many other drugs, due to factors commonly referred to as "enzyme induction" or "pharmacokinetic tolerance".

Accordingly, even before seeing the prolonged lactate reduction results of Example 2, the Applicant had scheduled a series of tests on the same test subjects who received the 60 mg/kg infusion described in Example 2. This second infusion test was designed solely to determine whether a second infusion of DCA would be cleared more rapidly, in people who had been previously exposed to DCA a few hours earlier.

Accordingly, all test subjects who received an 60 mg/kg intravenous infusion of DCA during the experiment described in Example 2 also received a second infusion of 30 mg/kg DCA, 8 hours later. For comparison, human beings who had received a saline placebo infusion received a second saline placebo infusion (and, once again, these human beings did not evidence any DCA in their blood stream, nor did they exhibit any significant reductions in serum lactate concentration).

Figure 4:
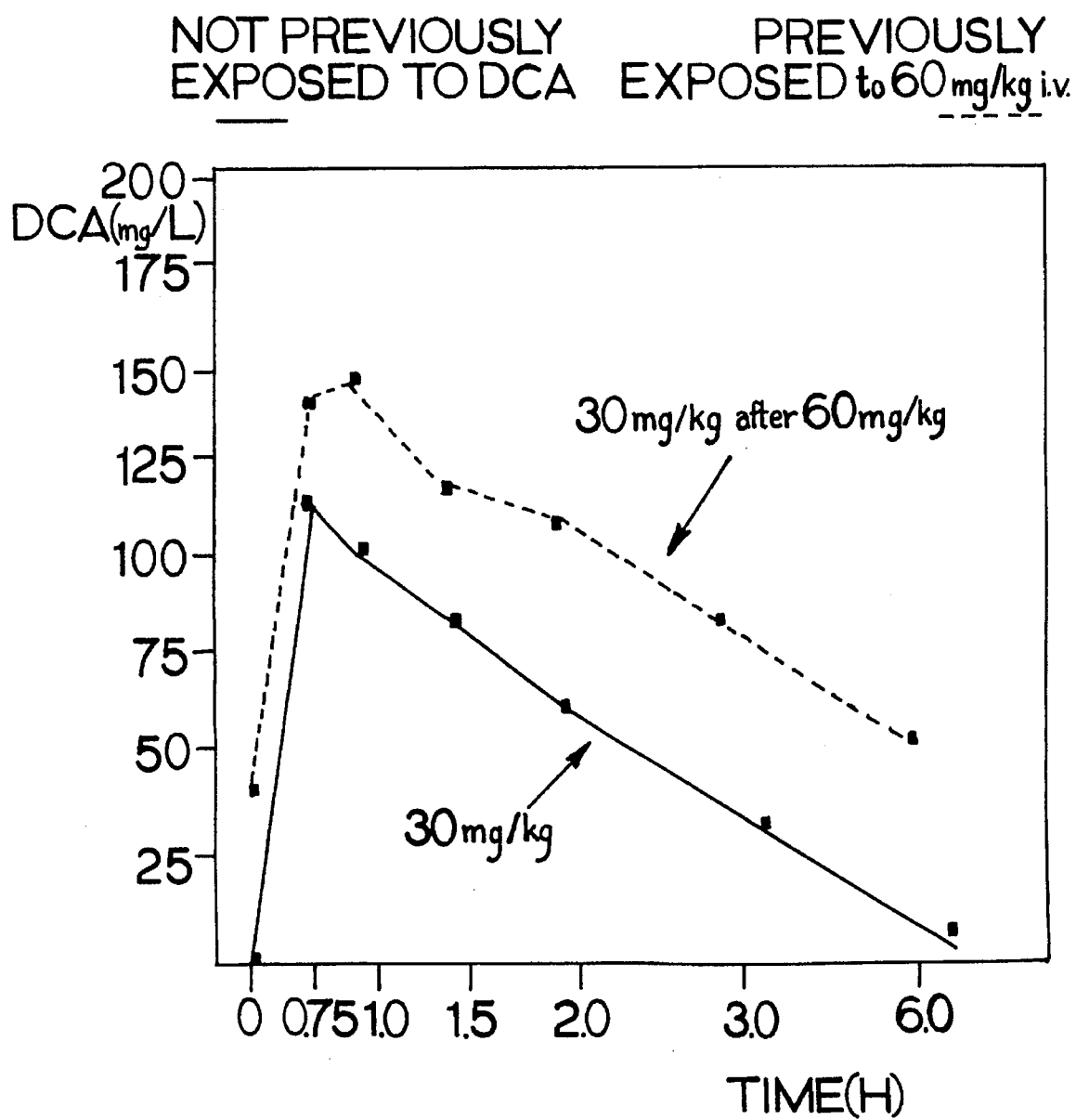
FIG. 4 indicates DCA clearance pharmacokinetics in both (1) patients that had not been previously injected with DCA, and (2) patients that had not been previously injected with DCA; the results indicate that prior administration of DCA does not cause a substantial change in DCA clearance pharmacokinetics.
Figure 5:
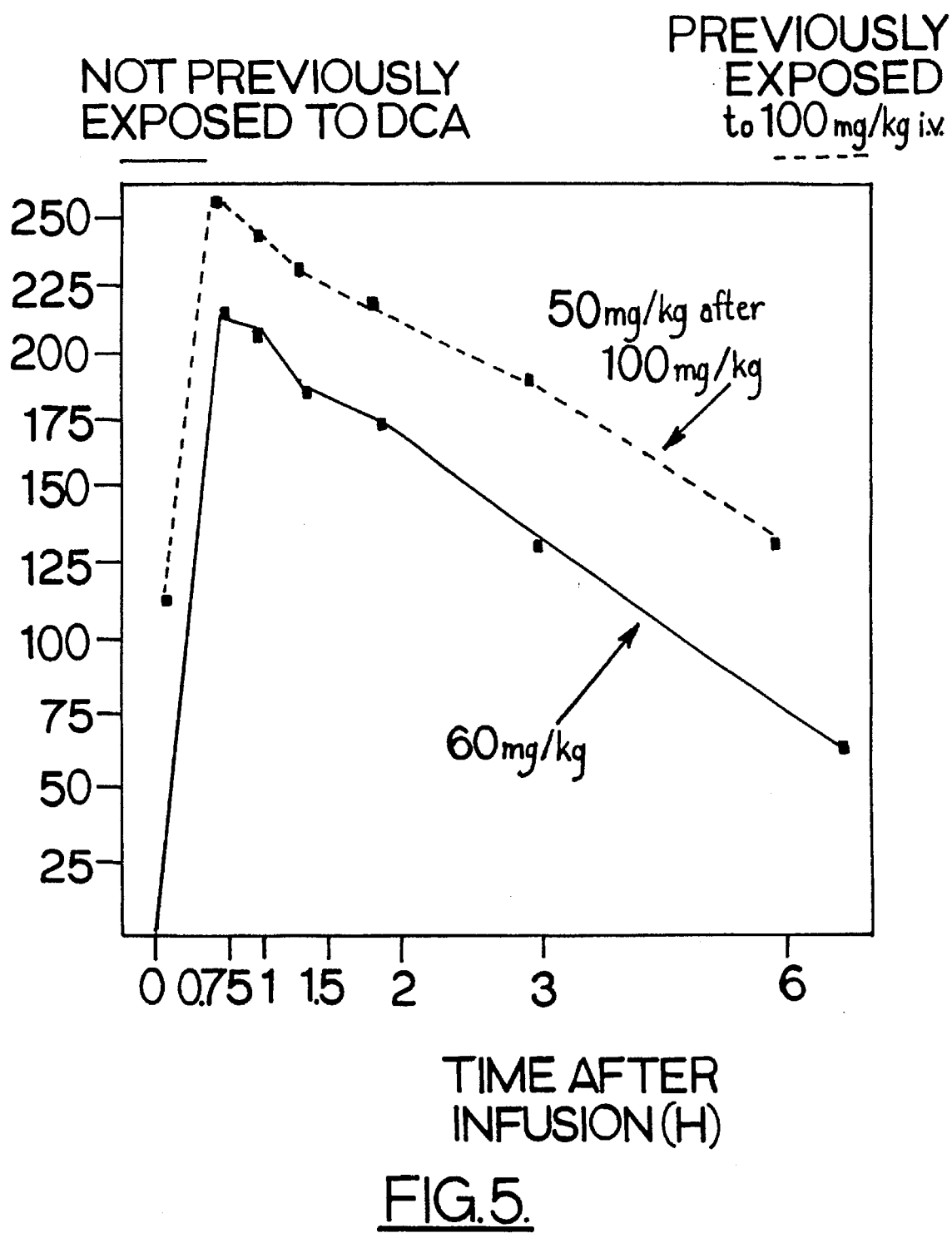
FIG. 5 also indicates DCA clearance pharmacokinetics in patients that had (or had not) been previously injected with DCA, at different dosage levels compared to FIG. 4.

The results, shown in FIG. 4, indicated that the pharmacokinetic clearance rates after a second infusion of DCA were comparable to the clearance of the same dose (30 mg/kg) by test subjects who had not been previously exposed to DCA, as described in Example 1.

EXAMPLE 5

A FURTHER EXAMPLE OF THE UNCHANGED ELIMINATION OF DCA AFTER PREVIOUS EXPOSURE TO THE AGENT

In some circumstances, even though an initial low dose of a drug will not hasten elimination of a subsequent dose, larger initial doses of the drug will do so; this effect is observed in, for example, barbital drugs.

Accordingly, to ensure that this effect would not occur when DCA was administered, an initial dose of 100 mg/kg NaDCA was infused into test subjects, and a second dose of 50 mg/kg was infused 8 hours later.

The dose of 100 mg/kg is the highest dose so far administered to human beings within 30 minutes. At this high rate of infusion, a number of subjects reported transient sedation or sleepiness, which lasted typically for about 20 minutes (a time period that corresponded to the highest plasma concentrations of DCA). This was not considered clinically significant and needed no treatment; it would be relatively unimportant in most of the pathological states that are proper subjects for treatment using DCA. However, the sedation side effect was regarded as creating a practical limit (100 mg/kg infused in 30 minutes or less) for tests on healthy volunteers.

A 50 mg/kg dose of DCA was administered after a 100 mg/kg dose had been administered 8 hours previously, using the procedures set forth in Example 4. The 50 mg/kg dose of DCA was cleared from the blood at a rate similar to the rate of clearance that occurred when a single dosage of 60 mg/kg was infused into previously unexposed test subjects, as described in Example 2.

EXAMPLE 6

PERSISTENCE OF THE EFFECTS OF DCA FOR MORE THAN 12 HOURS AFTER THE LAST DOSE

Nine of the test subjects in Example 3 who received an initial infusion of 100 mg/kg, received a second infusion of 50 mg/kg 8 hours later. Blood was samples periodically, up to 24 hours after the start of the first infusion. These values were compared to samples from nine control subjects who had received two saline placebo infusions.

The results from all three sets of patients (i.e., those receiving placebos only, those receiving 60 mg DCA followed by 30 mg DCA, and those receiving 100 mg DCA followed by 50 mg DCA) are in Table 1. Serum lactate values are in millimolar (mM) quantities and indicate mean values, followed by the standard error of the mean (SEM) for that treatment group.

TABLE 1

| LACTATE LEVELS IN PEOPLE RECEIVING DCA | | | |
|---|---|---|---|
| Treatment group: | Placebos | 60 + 30 | 100 + 50 |
| Baseline: | 0.92 ± 0.16 | 1.19 ± 0.24 | 0.84 ± 0.10 (a) |
| Just before second infusion: | 1.30 ± 0.15 | 0.72 ± 0.15 | 0.39 ± 0.04 (b) |
| 14 h after second infusion: | 1.43 ± 0.20 | 0.94 ± 0.12 | 0.32 ± 0.08 (c) |
| Levels of statistical significance: | | | |
| (b) vs. placebo | — | 0.009 | <0.001 |
| (c) vs. placebo | — | 0.021 | <0.001 |
| (b) vs. 60 + 30 | — | — | NS |
| (c) vs. 60 + 30 | — | — | 0.004 |

These results indicate that two infusions of DCA, eight hours apart, generated sustained and prolonged reductions in plasma lactate concentration for more than 12 hours after start of the second infusion, without any trend to return to baseline. This confirms that two doses of DCA per day are capable of generating a sustained reduction in blood lactate, over a full 24-hour period.

Thus, there has been shown and described a new method for administering dichloroacetate to human patients in a simpler, less intrusive, less expensive manner than previously known, using two injections per day in quantities that sustain a desirable level of lactate reduction over an entire 24 hour period or longer. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Abemayor, E., et al, "Effects of dichloroacetate on brain pyruvate dehydrogenase," *J Neurochem* 42:38–42 (1982)

Carraro, F., et al, "Effect of dichloroacetate on lactate concentration in exercising humans," *J. Appl Physiol* 66:591–597 (1989)

Coude, F. X., et al, "Dichloroacetate as treatment for congenital lactic acidosis," *New Eng J Med* 299:1365–1366 (1978)

Crabb, D. W., et al, "The metabolic effects of dichloroacetate," *Metabolism* 30:1024–1039 (1981)

Curry, S. H., et al, "Plasma concentrations and metabolic effects of intravenous sodium dichloroacetate," *Clin Pharmacol Ther* 37:89–93 (1985)

Evans, O.B., "Dichloroacetate tissue concentrations and its relationship to hypolactatemia and pyruvate dehydrogenase activation," *Biochem Pharmacol* 31: 3124–3126 (1982)

Evans, O. B., "Effects of dichloroacetate on brain tissue pyruvate dehydrogenase," *J Neurochem* 41:1052–1056 (1983)

Irisigler, K., et al, "Treatment of biguanide-induced lactic acidosis with dichloroacetate," *Arzneimittel Forschung* 29: 555–559 (1979)

Kodama, H., et al, "Renal effects of dichloroacetate in vivo," *Clin Chim Acta* 160: 265–271 (1986)

Kuroda, Y., et al, "Treatment of chronic congenital lactic acidosis by oral administration of dichloroacetate," *J Inher Metab Dis* 9: 244–252 (1986)

Ludvik, B., et al, "Effects of dichloroacetate and bicarbonate on hemodynamic parameters in healthy volunteers," *Clin Sci* 80:47–51 (1991)

Lukas, G., et al, "Biological disposition of sodium dichloroacetate in animals and humans after intravenous administration," *J Pharmaceut Sci* 69: 419–421 (1980)

Park, R. and Arieff, A. I., "Treatment of lactic acidosis with dichloroacetate in dogs," *J Clin Invest* 70: 853–862 (1982)

Ribes, G., et al, "Metabolic effects of sodium dichloroacetate," *Diabetes* 28: 852–856 (1979)

Stacpoole, P. W., et al, "Metabolic effects of dichloroacetate in patients with diabetes mellitus and hyperlipoproteinemia," *New Eng J Med* 298: 526–530 (1978)

Stacpoole, P. W., et al, "Toxicity of chronic dichloroacetate," *New Eng J Med* 300: 372 (1979)

Stacpoole, P. W., et al, "Treatment of lactic acidosis with dichloroacetate," *New Eng J Med* 309: 390–396 (1983)

Stacpoole, P. W., et al, "Dichloroacetate in the treatment of lactic acidosis," *Ann. Internal Med* 108: 58–63 (1988)

Stacpoole, P. W., "The pharmacology of dichloroacetate," *Metabolism* 38: 1124–1144 (1989)

Stacpoole, P. W. et al, "A controlled clinical trial of dichloroacetate for treatment of lactic acidosis in adults, " *New Eng J Med* 327: 1564–1569 (1992)

Toth, P. P., et al, "Transient improvement of congenital lactic acidosis in a male infant with pyruvate decarboxylase deficiency treated with dichloroacetate," *J Pediatr* 123: 427–430 (1993)

Wells, P. G., et al, "Metabolic effects and pharmacokinetics of intravenously administered dichloroacetate in humans," *Diabetologica* 19: 109–113 (1980)

Wolfe, R. R., et al, "Isotopic evaluation of the metabolism of pyruvate and related substrates in normal adult volunteers and severely burned children: effect of dichloroacetate and glucose infusion," *Surgery* 110: 54–67 (1991)

I claim:

1. A method of administering dichloroacetate to a human patient suffering from undesirably elevated levels of lactate in hypoxic tissue or circulating blood, comprising the step of injecting a physiologically acceptable salt of dichloroacetate into the patient twice over a 24-hour period, at dosages sufficient to sustain a substantial reduction in lactate concentration in the patient's blood for at least 24 hours.

2. The method of claim 1, wherein dichloroacetate is injected into the patient at quantities sufficient to sustain a substantial reduction in lactate concentration in the circulating blood for at least about 24 hours, despite clearance of substantially all dichloroacetate from the circulating blood in less than 24 hours.

3. The method of claim 1, wherein at least about 50 milligrams of dichloroacetate salt, per kilogram of body weight, are injected into the patient's bloodstream in each injection.

4. The method of claim 1, wherein the patient is suffering from an ischemic or hypoxic condition selected from the group consisting of stroke, heart attack, cardiac arrest, injury to central nervous system tissue, elevated intracranial pressure, suffocation, asphyxia, near-drowning, congenital lactic acidosis, and carbon monoxide poisoning.

5. The method of claim 1, wherein the patient is experiencing or anticipating surgery that disrupts normal physiological blood supply to at least one organ.

* * * * *